United States Patent
Kliss et al.

(10) Patent No.: US 7,348,029 B2
(45) Date of Patent: Mar. 25, 2008

(54) SURFACE-MODIFIED ZINC OXIDE FOR THE PRODUCTION OF NANOPARTICULATE DISPERSIONS

(75) Inventors: Rainer Kliss, Reinheim (DE); Ralf Elsässer, Augsburg (DE); Melita Heller, Düsseldorf (DE); Christian Umbreit, Düsseldorf (DE); Horst Hahn, Seeheim-Jugenheim (DE); Christian Kropf, Hilden (DE); Mete Berber, Ober-Ramstadt (DE); Victor Bulto Carulla, Barcelona (ES)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 273 days.

(21) Appl. No.: 10/872,664

(22) Filed: Jun. 21, 2004

(65) Prior Publication Data

US 2005/0048010 A1 Mar. 3, 2005

Related U.S. Application Data

(63) Continuation of application No. PCT/EP02/13852, filed on Dec. 6, 2002.

(30) Foreign Application Priority Data

Dec. 21, 2001 (DE) .............................. 101 63 256

(51) Int. Cl.
  *A61K 9/14* (2006.01)
  *A61K 9/16* (2006.01)
  *A61K 9/50* (2006.01)
  *A61K 33/32* (2006.01)
(52) U.S. Cl. ........................ 424/490; 424/489; 424/642
(58) Field of Classification Search ................ 424/489, 424/490, 641, 643, 642
See application file for complete search history.

(56) References Cited

U.S. PATENT DOCUMENTS

| | | | |
|---|---|---|---|
| 5,593,781 A | 1/1997 | Nass et al. | |
| 6,676,821 B1 | 1/2004 | Hempelmann et al. | |
| 6,710,091 B1 | 3/2004 | Womelsdorf et al. | |
| 2004/0033270 A1* | 2/2004 | Kropf et al. | 424/642 |
| 2004/0108220 A1 | 6/2004 | Stephan et al. | |

FOREIGN PATENT DOCUMENTS

| | | |
|---|---|---|
| DE | 1 165 574 | 3/1964 |
| DE | 199 07 704 A1 | 8/2000 |

(Continued)

OTHER PUBLICATIONS

U.S. Appl. No. 10/872,808, filed Jun. 21, 2004, Sauer et al.

(Continued)

*Primary Examiner*—Sreeni Padmanabhan
*Assistant Examiner*—Konata M. George
(74) *Attorney, Agent, or Firm*—Woodcock Washburn LLP

(57) ABSTRACT

The present invention relates to a surface-modified nanoscale zinc oxide, where the surface modification involves coating with an oligo- or polyethylene glycol acid. This surface-modified zinc oxide is characterized in that it forms stable dispersions in a liquid medium. In addition, the present invention relates to a process for the production of surface-modified zinc oxide, and also to a process for the production of nanoscale zinc oxide dispersions.

21 Claims, 2 Drawing Sheets

FOREIGN PATENT DOCUMENTS

| | | |
|---|---|---|
| EP | 1 112 964 A1 | 7/2001 |
| GB | 962 919 | 7/1964 |
| WO | WO 93/21127 A1 | 10/1993 |
| WO | WO 00/14302 A1 | 3/2000 |
| WO | WO 00/50503 A1 | 8/2000 |

OTHER PUBLICATIONS

Gmelins, vol. 32, 8th Edition, Erganzungsband, p. 772 (1956).

Guo et al., Synthesis and Characterization of Poly(vinylpyrrolidone)-Modified Oxide Nano-particles, vol. 12, pp. 2268-2274 (2000).

C. E. Krill et al., "Estimating grain-size distributions in nanocrystalline materials from X-ray diffraction profile analysis", Phil. Mag. A, vol. 77, No. 3, pp. 621-640 (1998).

L. Brus, "Electronic Wave Functions in Semiconductor Clusters: Experiment and Theory", J. Phys. Chem. vol. 90, pp. 2555-2560 (1986).

Mosmann, "Rapid Colorimetric Assay for Cellular Growth and Surival: Application to Proliferatio and Cytotoxicity Assays", Journal of Immunological Methods, vol. 65, pp. 55-63 (1983).

International Cosmetic Ingredient Dictionary and Handbook, 8th Edition, vol. 1, p. 527 (2000).

Liu et al., "Preparation of surface modified nanostructured ZnO and its photo-absorption characteristics", AN 2000:635354 (2000).

* cited by examiner

SURFACE-MODIFIED ZINC OXIDE FOR THE PRODUCTION OF NANOPARTICULATE DISPERSIONS

CROSS REFERENCE TO RELATED APPLICATIONS

This application is a continuation of PCT/EP02/13852, filed Dec. 6, 2002, which claims the benefit of DE 101 63 256.8, filed Dec. 21, 2001, the complete disclosures of which are hereby incorporated by reference in their entirety.

FIELD OF THE INVENTION

The present invention relates to a surface-modified nanoscale zinc oxide, where the surface modification involves coating with an oligo- or polyethylene glycol acid. This surface-modified zinc oxide is characterized in that it forms stable dispersions in a liquid medium. In addition, the present invention relates to a process for the production of surface-modified zinc oxide, and also to a process for the production of nanoscale zinc oxide dispersions. Such zinc oxides or zinc oxide dispersions can have various technical uses, such as, for example, in cosmetic formulations, as UV protection or as antimicrobial active ingredient.

BACKGROUND

The production of zinc oxide by dry and wet processes is known. The classic method of combusting zinc, which is known as a dry process (e.g. Gmelin Volume 32, 8th edition, supplementary volume, p. 772 ff.), produces aggregated particles with a broad size distribution. Although it is in principle possible to produce particle sizes in the submicrometer range by grinding processes, due to the low shear forces which can be achieved, it is not possible to achieve dispersions with average particle sizes in the lower nanometer range from such powders. Particularly finely divided zinc oxide is produced primarily wet-chemically by precipitation processes. The precipitation in aqueous solution generally produces hydroxide- and/or carbonate-containing materials, which have to be reacted thermally to give zinc oxide. The thermal after-treatment has an adverse effect on the finely divided nature since the particles are subjected to sintering processes which lead to the formation of aggregates which are micrometer sized and which can only be broken down incompletely into the primary particles by grinding.

Nanoparticulate metal oxides can be obtained, for example, by the microemulsion process. In this process, a solution of a metal alkoxide is added dropwise to a water-in-oil microemulsion. The hydrolysis of the alkoxides then takes place to give the nanoparticulate metal oxide in the inverse micelles of the microemulsion, the size of which is in the nanometer range. The disadvantages of this process are, in particular, the fact that the metal alkoxides are expensive starting materials, that emulsifiers have to be additionally used and that the production of the emulsions with particle sizes in the nanometer range represents a complex process step.

DE 199 07 704 describes a nanoscale zinc oxide produced by means of a precipitation reaction. In this reaction, the nanoscale zinc oxide is produced starting from a zinc acetate solution by means of alkaline precipitation. The zinc oxide which is centrifuged off can be redispersed to give a sol by adding methylene chloride. The zinc oxide dispersions produced in this way have the disadvantage that, due to a lack of surface modification, they do not have good long-term stability. Likewise due to the lack of surface modification, the production of zinc oxide dispersions is limited to dispersants which are not miscible with water. In addition, the description also mentions the possibility of producing colloidally disperse precipitated zinc oxide, in which a diol-polyol-water mixture using surface modifiers, such as, for example, triethanolamine, is used. In WO 00/50503, which claims the priority of this German application, an example of this is formulated where a mixture of these components is used in a ratio of ethylene glycol:water:triethanolamine in the weight ratio 2:1:0.55. Due to the high content of non-aqueous components, this mixture has significant disadvantages compared with the pure aqueous dispersions. Moreover, the zinc oxide particles here are not equipped with a permanent surface coating.

WO 00/50503 describes zinc oxide gels which comprise nanoscale zinc oxide particles with a particle diameter of ≦15 nm and which are redispersible sols. Here, the precipitations produced by basic hydrolysis of a zinc compound in alcohol or in an alcohol/water mixture are redispersed by adding dichloromethane or chloroform. A disadvantage here is that no stable dispersions are obtained in water or in aqueous dispersants.

In the publication from Chem. Mater "Synthesis and Characterization-of Poly(vinylpyrrolidone)-Modified Zinc Oxide Nanoparticles, Lin Guo and Shihe Yang, 2000, 12", bauxite zinc oxide nanoparticles are surface-coated with polyvinylpyrrolidone. The disadvantage here is that zinc oxide particles coated with polyvinylpyrrolidone are not dispersible in water.

WO 93/21127 describes a process for the production of surface-modified nanoscale ceramic powders. In this process, a nanoscale ceramic powder is surface-modified by applying a low molecular weight organic compound, for example propionic acid. This process cannot be used for the surface-modification of zinc oxide since the modification reactions are carried out in aqueous solution and zinc oxide dissolves in aqueous organic acids. For this reason, this process cannot be used for the production of zinc oxide dispersions; moreover, zinc oxide is also not specified as a possible starting material for nanoscale ceramic powders in this application.

SUMMARY

The object of the present invention was therefore to provide a nanoscale zinc oxide which permits the production of stable nanoparticulate dispersions in water or polar organic solvents. In order to be able to realize a use in, for example, cosmetic formulations on an industrial scale, it is necessary in this regard to start from commercially available, cost-effective starting materials for the production, where the production process should also permit by-products to be separated off easily. Irreversible aggregation of the particles should be avoided if possible so that a laborious grinding process can be avoided.

The invention is based on the finding that through a surface modification of zinc oxide with an oligo- or polyethylene glycol acid it is possible to achieve long-term stability of dispersions of the surface-modified zinc oxide.

DETAILED DESCRIPTION

Figure 1:
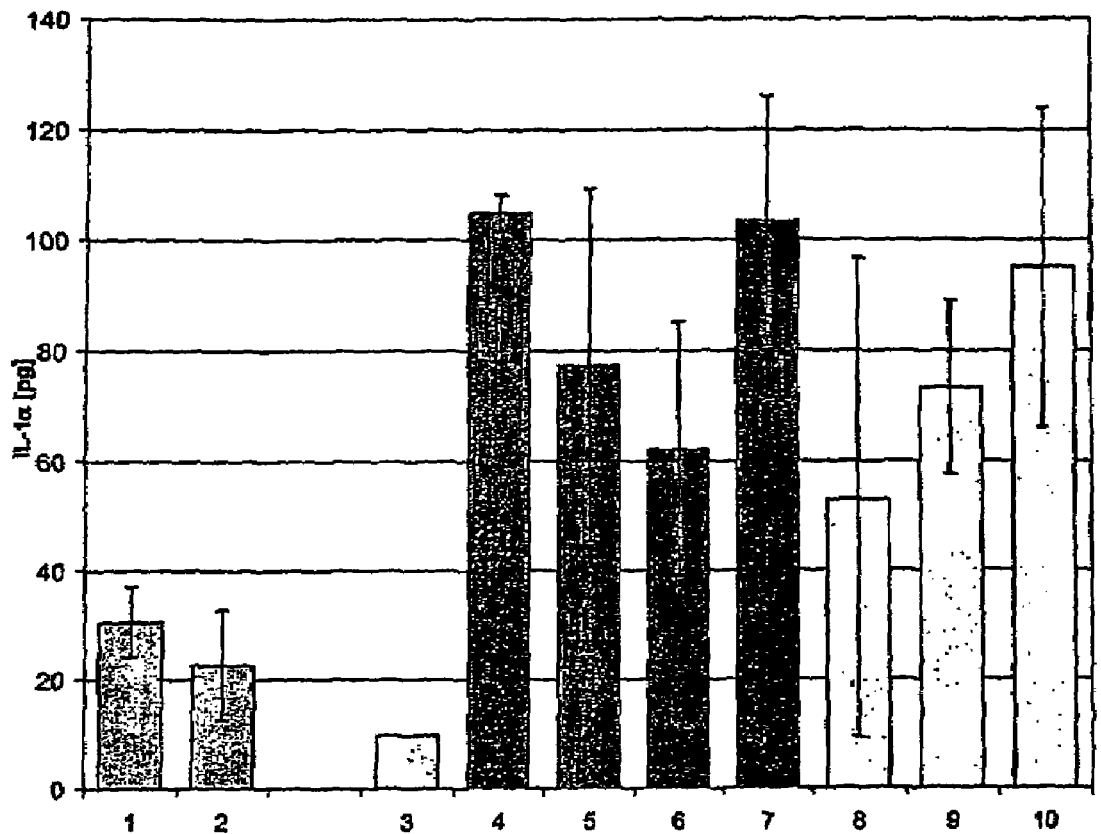
FIG. 1 shows Interleukin-1α release from the epidermis cultures after predamage for 1 hour with SDS 0.16% and subsequent incubation for 20 hours with the test substances.

The present invention therefore provides a surface-modified nanoparticulate zinc oxide which is characterized in that the surface modification involves coating with an oligo- or polyethylene glycol acid.

Surprisingly, this surface-modified nanoparticulate zinc oxide forms dispersions with long-term stability in a liquid medium. For the production of the surface-modified zinc oxides it is possible to use freely available zinc oxide powder, it being necessary for the primary crystallite size to be within the nanoparticulate range. This is understood as meaning particles which have a volume-weighted average crystallite diameter of less than 1000 nm, in particular particles which have a diameter of less than 500 nm. The volume-weighted average crystallite size can be determined by means of X-ray diffraction methods, in particular by means of a Scherrer analysis. The method is described, for example, in: C. E. Krill, R. Birringer: "Measuring average grain sizes in nanocrystalline materials", Phil. Mag. A 77, p. 621 (1998). According to this, the volume-weighted average crystallite size D can be determined by the relationship $$D = K\lambda/\beta \cos\theta$$

Here, $\lambda$ is the wavelength of the X-ray radiation used, $\beta$ is the full breadth at half the height of the reflection at diffraction position $2\theta$. K is a constant of the order of magnitude 1, whose precise value depends on the crystalline form. This uncertainty of K can be avoided by determining the linear broadening as the integral width $\beta_i$, where $\beta_i$ is defined as the area under the X-ray diffraction reflection, divided by its maximum intensity $I_0$:

$$\beta_i = \frac{1}{I_0} \int_{2\theta_1}^{2\theta_2} I(2\theta)\, d(2\theta)$$

Here, the parameters $2\theta_1$ and $2\theta_1$ are the minimum and maximum angle position of the Bragg reflection on the $2\theta$ axis. $I(2\theta)$ is the measured intensity of the reflection as a function of $2\theta$. Use of this relationship gives rise to the equation for determining the volume-weighted average crystallite size D:

$$D = \lambda/\beta_i \cos\theta$$

This zinc oxide can be surface-modified directly with an oligo- or polyethylene glycol acid, or firstly be subjected to an activation step. The surface activation of the zinc oxide can take place, for example, by admixing with a very diluted acid or base. Of particularly high suitability is the use of amorphous or crystalline zinc oxides which are obtained via an electrochemical process which is described in WO 00/14302. In this process, metals are dissolved anodically and precipitated as metal oxides at the cathode side. This is permitted through the use of organic electrolytes with a low water content with the simultaneous addition of conductive salts. If these zinc oxides are used, it has proven to be particularly advantageous if the zinc oxides are not dried before the surface modification, but used in the form of a zinc oxide suspension.

The invention further provides a process for the production of surface-modified nanoparticulate zinc oxide which is characterized in that untreated zinc oxide is suspended in a polar solvent, then admixed and heated with an oligo- or polyethylene glycol acid and the polar solvent is removed. Water may also be present in these polar organic solvents in any desired mixing ratio.

The invention further provides a process for the production of zinc oxide dispersions which is characterized in that surface-modified zinc oxide is introduced into water, into an organic solvent or into a mixture of an organic solvent and water and is dispersed by a suitable process.

The invention further provides zinc oxide dispersions which are produced by the process according to the invention given above and which are characterized in that the dispersions have a content of dispersed zinc oxide of from 0.001 to 50%.

The present invention further provides a cosmetic composition which comprises a zinc oxide surface-coated according to the invention or a zinc oxide dispersion.

The present invention further provides for the use of surface-modified zinc oxide or zinc oxide dispersions which have been produced by the process according to the invention:

for UV protection
as an antimicrobial active ingredient

According to a preferred embodiment of the present invention, the surface-modified zinc oxide is redispersible in a liquid medium and forms stable dispersions. This is particularly advantageous because the dispersions produced from the zinc oxide according to the invention do not have to be dispersed again prior to further processing, but can be processed directly.

According to a preferred embodiment of the present invention, the surface-modified zinc oxide is redispersible in polar organic solvents and forms stable dispersions. This is particularly advantageous since, as a result of this, uniform incorporation, for example into plastics or films, is possible.

According to a further preferred embodiment of the present invention, the surface-modified zinc oxide is redispersible in water, where it forms stable dispersions. This is particularly advantageous since this opens up the possibility of using the material according to the invention in, for example, cosmetic formulations, where the omission of organic solvents represents a major advantage. Also conceivable are mixtures of water and polar organic solvents.

In a further preferred embodiment of the present invention, the oligo- or polyethylene glycol acid for the surface modification of the zinc oxide corresponds to the general form R—$CH_2$—(O—$CH_2$—$CH_2$)$_n$—O—$CH_2$-COOH, where n is an integer from 0 to 40. This is particularly advantageous since, by using a compound of this type, on the one hand redispersibility in polar organic solvents and in water becomes possible, however, on the other hand, unlike the use of fatty acids otherwise used for this purpose, the nanoparticulate zinc oxides are dissolved.

According to a further particularly preferred embodiment of the present invention, the radical R is chosen from H, $CH_3$, $C_2H_5$, $C_3H_7$, $CH(CH_3)_2$, OH, $NH_2$, COOH, $CONH_2$, $CO_2CH_3$, $CO_2C_2H_5$, $CO_2C_3H_7$ and $CO_2$ $CH(CH_3)_2$. This is particularly advantageous since, when choosing these substituents, on the one hand, the surface modifier adheres well to the surface of the nanoparticulate zinc oxide and, on the other hand, the steric and electrostatic properties produce particularly uniform surface modifications.

According to a further preferred embodiment of the present invention, the surface modification of the zinc oxide involves an oligo- and/or polyethylene glycol diacetic acid of the general formula HOOC—$CH_2$—(O—$CH_2$—$CH_2$)$_n$—

O—$CH_2$—COOH, where n is an integer from 0 to 40. The use of compounds of this type is particularly advantageous since, as a result of them, on the one hand a firm bond to the nanoparticulate zinc oxide is achieved and on the other hand good redispersibility in polar organic solvents and in water is ensured. A further advantage of this compound category is that many representatives of the oligo- and/or polyethylene glycol diacetic acid can be used in cosmetic formulations since they have no toxicity and have already been approved.

According to a further particularly preferred embodiment of the present invention, the surface of the zinc oxide particles is modified with polyethylene glycol diacid 600. This is particularly advantageous because polyethylene glycol diacid 600 (where n=11 in the general formula HOOC—$CH_2$—(O—$CH_2$—$CH_2$)$_n$—O—$CH_2$—COOH) has already been approved for cosmetic purposes and moreover, even a relatively small amount of this agent is enough to achieve good redispersibility of the modified zinc oxide.

According to a particularly preferred embodiment of the present invention, the surface of the zinc oxide particles is modified with 2-[2-(2-methoxyethoxy)ethoxy]acetic acid. The use of this substance for the surface modification of nanoparticulate zinc oxide is therefore particularly advantageous because this substance is on the one hand very cost-effective and, furthermore, has very good surface adhesion.

According to a preferred embodiment of the present invention, the surface-modified zinc oxide particles have a diameter from 1 to 200 nm. This is particularly advantageous since good redispersibility is ensured within this size distribution.

According to a particularly preferred embodiment of the present invention, the zinc oxide nanoparticles have a diameter from 2 to 50 nm, very particularly preferably 3 to 10 nm. This size range is particularly advantageous since, following the redispersion of such zinc oxide nanoparticles, the resulting dispersions are transparent and thus, for example, do not influence the coloration when added to cosmetic formulations. Moreover, this also gives rise to the possibility of use in transparent films. If the zinc oxide dispersions are to be used as UV absorbers, it is advisable to use particles with a diameter of more than 5 nm since below this limit there is a shift in the absorption edge in the short-wave region (L. Brus, J. Phys., Chem. (1986), 90, 2555-2560).

The present invention further provides a process for the production of surface-modified zinc oxide, which is characterized in that the untreated zinc oxide is suspended in a polar solvent, then admixed and heated with an oligo- or polyethylene glycol acid for the surface modification and then the polar solvent is removed. A polar solvent is understood here as meaning both polar organic solvent, such as water and likewise mixtures of organic polar solvents and water in any desired ratios. Oligo- or polyethylene glycol acids suitable for the surface modification have the general form R—$CH_2$—(O—$CH_2$—$CH_2$)$_n$—O—$CH_2$—COOH, where n is an integer from 0 to 40 and R is chosen from H, $CH_3$, $C_2H_5$, $C_3H_7$, $CH(CH_3)_2$, OH, $NH_2$, COOH, $CONH_2$, $CO_2CH_3$, $CO_2C_2H_5$, $CO_2C_3H_7$ and $CO_2$ $CH(CH_3)_2$. Of particularly high suitability here are oligo- and/or polyethylene glycol diacetic acids of the general formula HOOC—$CH_2$—(O—$CH_2$—$CH_2$)$_n$—O—$CH_2$—COOH, where n is an integer from 0 to 40. A likewise preferred surface modifier for carrying out the process according to the invention is 2-[2-(2-methoxyethoxy)ethoxy]acetic acid. The advantage of this process according to the invention is that the products obtained are surface-modified zinc oxides which are very readily redispersible in a liquid medium and produce stable dispersions.

According to a particularly preferred embodiment of the process according to the invention, the solvent is removed by evaporation under atmospheric pressure or subatmospheric pressure, by freezing, freeze-drying, filtering and subsequent drying or drying at elevated temperature at atmospheric pressure or preferably at reduced pressure. This is particularly advantageous since, by virtue of this, the process is on the one hand accelerated and, on the other hand, gentle handling of the surface-modified, nanoparticulate zinc oxide is ensured, and solvent recovery is possible.

The present invention further provides a process for the production of zinc oxide dispersions which is characterized in that a zinc oxide surface-modified according to the invention is introduced into water, into an organic solvent or into a mixture of an organic solvent and water and is dispersed by a suitable process. Processes suitable for this purpose may be stirring, shaking, ultrasound treatment, heating and/or use of commercial dispersion apparatuses such as Ultra-Turrax, dissolvers, bead mills. This is particularly advantageous since dried zinc oxide powder surface-modified according to the invention can also be used in this process and be virtually completely redispersed again in the specified solvents or solvent mixtures. By virtue of this, when using the same starting substance, the dispersant can be chosen to produce different types of zinc oxide dispersions which are matched to the varying fields of use.

According to a preferred embodiment of the process according to the invention for the production of zinc oxide dispersions, an organic solvent with a dipole moment of $\geq 0.35$ μ/D is used. This is particularly advantageous since, by choosing a dispersant with such a dipole moment, on the one hand the long-term stability of the dispersions is ensured and, on the other hand, zinc oxide dispersions are thereby produced which are suitable, for example, for use in plastics.

According to a further preferred embodiment of the process according to the invention for the production of zinc oxide dispersions, the organic solvent is chosen, or a mixture, from methanol, n-propanol, isopropanol, acetone, diethyl ether, dimethyl sulfoxide, tetrahydrofuran, methylene chloride, trichloromethane, ethanol, ethyl acetate, isobutyl acetate and/or toluene. This is particularly advantageous since, by virtue of this process, zinc oxide dispersions in liquids of different physical properties can be produced, giving rise to a broad application spectrum for further uses of these zinc oxide dispersions. Relevant physical properties of the solvent are the miscibility in water, proticity/aproticity, dipole moment, boiling temperature or melting point.

The present invention further provides zinc oxide dispersions which have been produced by an abovementioned process and which are characterized in that the dispersions have a content of dispersed zinc oxide of from 0.001 to 50% by weight. This is particularly advantageous since, by virtue of this, zinc oxide dispersions with a broad concentration range are provided and are thus suitable for diverse intended uses.

According to a preferred embodiment of the zinc oxide dispersions according to the invention, the dispersions have a content of dispersed zinc oxide of from 0.1 to 10% by weight, particularly preferably 1 to 5% by weight. Dispersions with such a content of zinc oxide have the particular advantage that, even in unfavorable external conditions, they remain stable and there is no precipitation of the dispersed oxide. Unfavorable circumstances in this connection are ambient temperatures in the region of more than +/−10° C. deviation from room temperature or mechanical stresses, such as vibrations or stirring.

A particularly preferred embodiment of the zinc oxide dispersions according to the invention is characterized in that the dispersions are largely transparent. This is particularly advantageous since, by virtue of this, the zinc oxide dispersions have no influence on the coloration when incorporated into other products, such as, for example, plastic moldings. In particular, the zinc oxide dispersions can be used in films since they likewise do not impair the transparency of these films.

The present invention further provides a process for the surface coating with the zinc oxide surface-modified according to the invention, or a dispersion thereof, which is characterized in that a dispersion of the zinc oxide particles surface-modified according to the invention is applied to the surface to be coated and the dispersant is then removed. Removal of the dispersant can be completed in various ways: heating, stripping off the dispersant under reduced pressure, possibly with simultaneous heating, freeze-drying, air drying, hot-air drying, UV and infrared drying or high-frequency drying. The coating process can also be repeated a number of times if thicker layers are desired. The particular advantage of the thinner layers is the transparency for visible light. For example, thin zinc oxide coatings for optical devices, such as lenses, in particular also spectacles, produce an invisible UV broadband filter which is virtually 100% permeable for visible light and does not therefore lead to color shifts.

According to a preferred embodiment of the process according to the invention for the surface coating, a doping agent is added to the zinc oxide dispersion prior to application to the surface to be coated. Suitable doping agents for zinc oxide are, in particular, metal ions with one electron more or one electron less on the external shell. Main group metals and sub-group metals in oxidation state +III are particularly suitable. Boron(III), aluminum(III), gallium(III) and indium(III) are very particularly preferred. These metals can be added to the dispersion in the form of soluble salts, the choice of metal salt being dependent on whether it dissolves in the dispersant in the desired concentration. In the case of aqueous dispersions, many inorganic salts or else complexes are suitable, such as carbonates, halides, salts with EDTA, nitrates, salts with EDTA, acetyl acetonate etc. Doping with precious metals, such as palladium, platinum, gold, etc. is likewise possible. The donor concentration can be up to 5%. Doped zinc oxide coatings are suitably preferable for use as transparent electrodes for liquid crystal displays, flat panel displays, electrochromic windows (switchable light transmittance), photovoltaic solar cells or heatable mirrors.

According to a particularly preferred embodiment of the surface coating process according to the invention, the zinc oxide dispersion is applied to the substrate to be coated by means of a spin coater. To this end, the workpiece to be coated is inserted into the spin coater, brought to a certain starting speed and the zinc oxide dispersion is placed onto the substrate. Alternatively, the dispersion can also be applied to the substrate directly before or at exactly the same time as the spin coater is switched on. The spin coater then also performs a speed program, which is matched individually to the workpiece to be coated. This is a necessary adaptation process customary in the art which depends on the nature of the surface of the substrate (roughness, wettability, size, etc.) and on the properties of the coating composition (viscosity, wetting, density etc.). The rotational speeds usually oscillate in the range between a few hundred to a few thousand revolutions per minute. In this process, by means of a program control, the speed during spinning can be varied if this leads to a better coating. For example, for the case that the dispersion is applied to the stationary substrate, the speed is increased slowly after the spin coater has been switched on, in order to achieve a more uniform distribution of the coating composition.

By applying the layer by means of a spin coater, some of the dispersant is removed simultaneously by evaporation; this can be further intensified by simultaneously applying a vacuum during spinning. The layers which are produced using this process in a spinning operation have a thickness of from about 20 to 300 nm. The thickness can be influenced by the content of zinc oxide in the dispersion and through the choice of solvent/dispersant. A high mass percentage content of surface-modified zinc oxide increases the layer thickness during the spinning operation; as does choosing a dispersant with a relatively high viscosity. Moreover, these layers are characterized by a very uniform layer thickness and low degree of roughness. It is thus possible to produce layers which have a surface roughness of less than 1 nm. As a result of the low surface roughness and uniform thickness which can be achieved by this process, the coatings have very homogeneous optical and electrical properties.

The production of thicker layers in a spinning operation is, however, likewise possible, although these are no longer completely transparent. For example, it is possible to produce layers up to 1.2 µm in thickness. Alternatively to the spincoating, the coating can also be achieved by immersion or spraying on a zinc oxide dispersion.

According to a further particularly preferred embodiment of the coating process according to the invention, the already coated surface is then heated to a temperature between 100° C. and 1000° C. This is preferably carried out with the exclusion of oxygen or under a reducing atmosphere ($H_2$ or $H_2$-containing). The heating time is between 10 minutes and 6 hours. The heating is particularly advantageous because it enables, on the one hand, dispersant residues to be removed and, on the other hand, possible mechanical strains in the coating to heal. If doped zinc oxide layers are produced, then heating to a temperature of more than 300° C. is advantageous since above about this temperature, incorporation of the dopant into the zinc oxide lattice takes place within a relatively short time. It may also be advantageous to subject the surface coating to higher temperatures in order, for example, to remove the dopant and/or the anion of the dopant (e.g. by oxidation). Upon heating under a reducing atmosphere, precious metal precursors may, for example, be reduced to the metal.

A heating up to the proximity of the melting point of zinc oxide may likewise be advantageous for sintering together the individual nanoparticles to give a continuous layer.

According to a further particularly preferred embodiment of the surface coating process according to the invention, electrically conductive surfaces and layers are produced via this process. The advantages resulting therefrom have already been explained in detail above.

The present invention further provides a cosmetic composition which comprises a zinc oxide surface-modified according to the invention or a zinc oxide dispersion. This is particularly advantageous since, due to the fine distribution of the zinc oxide particles, they are able to develop their skin-calming effect more effectively. In this regard, a comparative experiment (example 3) was carried out in comparison with standard commercial skin-calming compositions. The improved effect compared with customary skin-calming active ingredients is clearly evident here. A further advantage is that, due to the small particle size, when applying to, for example, the skin, no rubbing effect arises, but a gentle application is possible, which brings about a pleasant feel on the skin.

According to a further embodiment of the cosmetic composition, the latter serves for the care or the protection of the skin, in particular for protection against the sun and/or for care during exposure to sunlight and is present in the form of an emulsion, a dispersion, a suspension, an aqueous surfactant preparation, a milk, a lotion, a cream, a balsam, an ointment, a gel, a granulate, a powder, a stick preparation, such as, for example, a lipstick, a foam, an aerosol or a spray. Such formulations are highly suitable for topical preparations. Suitable emulsions are oil-in-water emulsions and W/O emulsions or microemulsions. This is particularly advantageous since, through the use in sunscreen compositions, the UV-absorbing and the skin-calming effect of the zinc oxide can be used simultaneously. Moreover, the zinc oxide surface-modified according to the invention is highly suitable for use in sunscreen compositions since the particles can be produced in a size which appears transparent to the human eye. As a result, there is no white smear on the skin during application. A further advantage is the fact that zinc oxide is a UV broadband filter whose UV absorption behavior allows sunscreen compositions to be provided which requires no further chemical UV filter substances. As a result, the risk of skin irritations or allergic reactions as a result of decomposition products of chemical filters or as a result of these substances themselves can be avoided, which considerably increases the general compatibility of a sunscreen composition formulated in this way.

The cosmetic composition is usually used for topical application to the skin. Topical preparations are understood here as meaning those preparations which are suitable for applying the active ingredients to the skin in fine distribution and preferably in a form which can be absorbed by the skin. Suitable for this purpose are, for example, aqueous and aqueous-alcoholic solutions, sprays, foams, foam aerosols, ointments, aqueous gels, emulsions of O/W or W/O type, microemulsions or cosmetic stick preparations.

According to a preferred embodiment of the cosmetic composition according to the invention, the composition comprises a carrier. Preferred carriers are water, a gas, a water-based liquid, an oil, a gel, an emulsion or microemulsion, a dispersion or a mixture thereof. Said carriers exhibit good skin compatibility. Aqueous gels, emulsions or microemulsions are particularly advantageous for topical preparations.

Emulsifiers which can be used are nonionogenic surfactants, zwitterionic surfactants, ampholytic surfactants or anionic emulsifiers. The emulsifiers may be present in the composition according to the invention in amounts of from 0.1 to 10% by weight, preferably 1 to 5% by weight, based on the composition.

The nonionogenic surfactant which may be used is, for example, a surfactant from at least one of the following groups:

addition products of from 2 to 30 mol of ethylene oxide and/or 0 to 5 mol of propylene oxide onto linear fatty alcohols having 8 to 22 carbon atoms, onto fatty acids having 12 to 22 carbon atoms and onto alkylphenols having 8 to 15 carbon atoms in the alkyl group;

$C_{12/18}$-fatty acid mono- and diesters of addition products of from 1 to 30 mol of ethylene oxide onto glycerol;

glycerol mono- and diesters and sorbitan mono- and diesters of saturated and unsaturated fatty acids having 6 to 22 carbon atoms and ethylene oxide addition products thereof;

alkyl mono- and oligoglycosides having 8 to 22 carbon atoms in the alkyl radical and ethoxylated analogs thereof;

addition products of from 15 to 60 mol of ethylene oxide onto castor oil and/or hydrogenated castor oil;

polyol and in particular polyglycerol esters, such as, for example, polyglycerol polyricinoleate, polyglycerol poly-12-hydroxystearate or polyglycerol dimerate. Likewise suitable are mixtures of compounds of two or more of these classes of substance;

addition products of from 2 to 15 mol of ethylene oxide onto castor oil and/or hydrogenated castor oil;

partial esters based on linear, branched, unsaturated or saturated $C_{6/22}$-fatty acids, ricinoleic acid, and 12-hydroxystearic acid and glycerol, polyglycerol, pentaerythritol, dipentaerithritol, sugar alcohols (e.g. sorbitol), alkylglucosides (e.g. methylglucoside, butylglucoside, lauryl glucoside) and polyglucosides (e.g. cellulose);

mono-, di- and trialkyl phosphates, and mono-, di- and/or tri-PEG alkyl phosphates and salts thereof;

wool wax alcohols;

polysiloxane-polyalkyl-polyether copolymers and corresponding derivatives;

mixed esters of pentaerythritol, fatty acids, citric acid and fatty alcohol according to German patent 1165574 and/or mixed esters of fatty acids having 6 to 22 carbon atoms, methyl glucose and polyols, preferably glycerol or polyglycerol and polyalkylene glycols betaines ester quats In addition, emulsifiers which may be used are zwitterionic surfactants. Zwitterionic surfactants are those surface-active compounds which carry at least one quaternary ammonium group and at least one carboxylate or one sulfonate group in the molecule. Particularly suitable zwitterionic surfactants are the so-called betaines, such as the N-alkyl-N,N-dimethylammonium glycinates, for example cocoalkyldimethylammonium glycinate, N-acylaminopropyl-N,N-dimethylammonium glycinates, for example the cocacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethyl hydroxyethylcarboxymethylglycinate. Particular preference is given to the fatty acid amide derivative known under the CTFA name *Cocamidopropyl Betaine*.

Likewise suitable emulsifiers are ampholytic surfactants. Ampholytic surfactants are understood as meaning those surface-active compounds which, apart from a $C_{8/18}$-alkyl-acyl group in the molecule, contain at least one free amino group and at least one —COOH or —SO$_3$H group and are able to form internal salts. Examples of suitable ampholytic surfactants are N-alkylglycines, N-alkylpropionic acids, N-alkylaminobutyric acids, N-alkylaminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 carbon atoms in the alkyl group. Particularly preferred ampholytic surfactants are N-cocoalkylaminopropionate, cocoacylaminoethylaminopropionate and $C_{12/18}$-acylsarcosine. Besides the ampholytic emulsifiers, quaternary emulsifiers are also suitable, particular preference being given to those of the ester quat type, preferably methyl-quaternized difatty acid triethanolamine ester salts. Furthermore, anionic emulsifiers which may be used are alkyl ether sulfates, monoglyceride sulfates, fatty acid sulfates, sulfosuccinates and/or ethercarboxylic acids.

Suitable oil bodies are Guerbet alcohols based on fatty alcohols having 6 to 18, preferably 8 to 10, carbon atoms, esters of linear $C_6$-$C_{22}$-fatty acids with linear $C_6$-$C_{22}$-fatty alcohols, esters of branched $C_6$-$C_{13}$-carboxylic acids with linear $C_6$-$C_{22}$-fatty alcohols, esters of linear $C_6$-$C_{22}$-fatty acids with branched alcohols, in particular 2-ethylhexanol, esters of linear and/or branched fatty acids with polyhydric alcohols (such as, for example, propylene glycol, dimerdiol or trimertriol) and/or Guerbet alcohols, triglycerides based on $C_6$-$C_{10}$-fatty acids, liquid mono-/di-/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, vegetable oils, branched primary alcohols, substituted cyclohexanes, linear $C_6$-$C_{22}$-fatty alcohol carbonates, Guerbet carbonates, esters of benzoic acid with linear and/or branched $C_6$-$C_{22}$-alcohols (e.g. Finsolv® TN), dialkyl ethers, ring-opening products of epoxidized fatty acid esters with polyols, silicone oils and/or aliphatic or naphthenic hydrocarbons. In addition, oil bodies which may be used are also silicone compounds, for example dimethylpolysiloxanes, methylphenylpolysiloxanes, cyclic silicones, and amino-, fatty acid-, alcohol-, polyether-, epoxy-, fluoro-, alkyl- and/or glycoside-modified silicone compounds, which may be present either in liquid form or in resin form at room temperature. The oil bodies may be present in the compositions according to the invention in amounts of from 1 to 90% by weight, preferably 5 to 80% by weight, and in particular 10 to 50% by weight-based on the composition.

According to a particularly preferred embodiment, the composition according to the invention comprises further UV light protection filters in the form of soluble compounds or other pigments.

Although, as has already been described above, it is possible to use these zinc oxide particles according to the invention to create a sunscreen composition which achieves good UV absorption properties without further UV filter substances, it may be desired in individual cases to add further UV filter substances to the cosmetic composition or the sunscreen composition. This may be required when, for example, particular emphasis is to be placed on the filter performance. One or more further UV light protection filters may be added to the composition according to the invention.

In the case of the soluble compounds, UV light protection filters are understood as meaning organic substances which are able to absorb ultraviolet rays and give off the absorbed energy again in the form of longer-wave radiation, e.g. heat. The organic substances may be oil-soluble or water-soluble.

As oil-soluble UV-B filters it is possible to use, for example, the following substances:

3-benzylidenecamphor and derivatives thereof, e.g. (3-(4-methylbenzylidene)camphor; 4-aminobenzoic acid derivatives, preferably 2-ethylhexyl 4-(dimethylamino) benzoate, 2-octyl 4-(dimethylamino)benzoate and amyl 4-(dimethylamino)benzoate; esters of cinnamic acid, preferably 2-ethylhexyl 4-methoxycinnamate, propyl 4-methoxycinnamate, isoamyl 4-methoxycinnamate, isopentyl 4-methoxycinnamate, 2-ethylhexyl 2-cyano-3-phenylcinnamate (octocrylene); esters of salicylic acid, preferably 2-ethylhexyl salicylate, 4-isopropylbenzyl salicylate, homomenthyl salicylate; derivatives of benzophenone, preferably 2-hydroxy-4-methoxybenzophenone, 2-hydroxy-4-methoxy-4'-methylbenzophenone,-2,2'-dihydroxy-4-methoxybenzophenone; esters of benzalmalonic acid, preferably di-2-ethylhexyl 4-methoxybenzmalonate; triazine derivatives, such as, for example, 2,4,6-trianilino-(p-carbo-2'-ethyl-1'-hexyloxy)-1,3,5-triazine (octyltriazone) and dioctyl butamidotriazone (Uvasorb® HEB); propane-1,3-diones, such as, for example 1-(4-tert-butylphenyl)-3-(4'-methoxyphenyl)propane-1,3-dione.

Suitable water-soluble substances are 2-phenylbenzimidazole-5-sulfonic acid and the alkali metal, alkaline earth metal, ammonium, alkylammonium, alkanolammonium and glucammonium salts thereof; sulfonic acid derivatives of benzophenones, preferably 2-hydroxy-4-methoxybenzophenone-5-sulfonic acid and its salts; sulfonic acid derivatives of 3-benzylidenecamphor, such as, for example, 4-(2-oxo-3-bornylidenemethyl)benzenesulfonic acid and 2-methyl-5-(2-oxo-3-bornylidene)sulfonic acid and salts thereof.

Particular preference is given to the use of esters of cinnamic acid, preferably 2-ethylhexyl 4-methoxycinnamate, isopentyl 4-methoxycinnamate, 2-ethylhexyl 2-cyano-3-phenylcinnamate (octocrylene). Furthermore, the use of derivatives of benzophenone, in particular 2-hydroxy-4-methoxybenzophenone, 2-hydroxy-4-methoxy-4'-methylbenzophenone, 2,2'-dihydroxy-4-methoxybenzophenone, and the use of propane-1,3-diones, such as, for example, 1-(4-tert-butylphenyl)-3-(4'-methoxyphenyl)propane-1,3-dione is preferred.

Suitable typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane or 1-phenyl-3-(4'-isopropylphenyl)propane-1,3-dione. The UV-A and UV-B filters may of course also be used in mixtures.

Further light protection filters which may be used are, however, also other insoluble pigments, e.g. finely disperse metal oxides and/or salts, such as, for example, titanium dioxide, iron oxide, aluminum oxide, cerium oxide, zirconium oxide, silicates (talc), barium sulfate and zinc stearate. The particles here should have an average diameter of less than 100 nm, preferably between 5 and 50 nm and in particular between 15 and 30 nm.

Besides the two aforementioned groups of primary photoprotective substances, it is also possible to use secondary photoprotective agents of the antioxidant type, which interrupt the photochemical reaction chain which is triggered when UV radiation penetrates into the skin. Typical examples thereof are superoxide dismutase, tocopherols (vitamin E) and ascorbic acid (vitamin C).

The total amount of photoprotective agents in the sunscreen composition according to the invention is usually 1 to 20% by weight, preferably 5 to 15% by weight. The composition according to the invention as such can comprise 1 to 95% by weight, preferably 5 to 80% by weight and in particular 10 to 60% by weight, of water.

According to a particularly preferred embodiment, the cosmetic composition according to the invention further comprises care substances, further cosmetic active ingredients and/or auxiliaries and additives. The further cosmetic active ingredients used are, in particular, skin moisturizers, antimicrobial substances and/or deodorizing or antiperspirant substances. This has the advantage that further desired effects can be achieved which contribute to the care or treatment of the skin or, for example, increase the wellbeing of the user of the cosmetic composition upon use of this composition.

Thus, besides the carrier, the surface-modified zinc oxide, water and physiologically suitable solvents, the cosmetic composition may also comprise, inter alia, care constituents, such as, for example, oils, waxes, fats, refatting substances, thickeners, emulsifiers and fragrances. A high content of care substances is advantageous particularly for topical prophylactic or cosmetic treatment of the skin. It is particularly advantageous if the composition also comprises further care components besides the animal and vegetable fats and oils which likewise have a care effect in many cases. The group of care active ingredients which can be used includes, for example, fatty alcohols having 8-22 carbon atoms, in particular fatty alcohols of natural fatty acids; animal and vegetable protein hydrolysates, in particular elastin, collagen, keratin, milk-protein, soya protein, silk protein, oat protein, pea protein, almond protein and wheat protein hydrolysates; vitamins and vitamin precursors, in particular those of vitamin groups A and B; mono-, di- and oligosaccharides; plant extracts; honey extracts; ceramides; phospholipids; vaseline, paraffin and silicone oils; fatty acid and fatty alcohol esters, in particular the monoesters of fatty acids with alcohols having 3-24 carbon atoms.

The vitamins, provitamins or vitamin precursors to be used with preference in the composition according to the invention include, inter alia: vitamins, provitamins and vitamin precursors from the groups A, C, E and F, in particular 3,4-didehydroretinol (vitamin $A_2$), β-carotene (provitamin of vitamin $A_1$), ascorbic acid (vitamin C), and the palmitic esters, glucosides or phosphates of ascorbic acid, tocopherols, in particular α-tocopherol and its esters, e.g. the acetate, the nicotinate, the phosphate and the succinate; also vitamin F, which is understood as including essential fatty acids, in particular linoleic acid, linolenic acid and arachidonic acid; vitamin A and its derivatives and provitamins advantageously exhibit a particular skin-smoothing effect.

The vitamins, provitamins or vitamin precursors of the vitamin B group to be used with preference in the composition according to the invention, or derivatives thereof and the derivatives of 2-furanone include, inter alia: Vitamin $B_1$, trivial name thiamine, chemical name 3-[(4'-amino-2'-methyl-5'-pyrimidinyl)-methyl]-5-(2-hydroxyethyl)-4-methylthiazolium chloride. Preference is given to using thiamine hydrochloride in amounts of from 0.05 to 1% by weight, based on the total composition; Vitamin $B_2$, trivial name riboflavin, chemical name 7,8-dimethyl-10-(1-D-ribityl) benzo[g]pteridine-2,4-(3H, 10H)-dione. Riboflavin occurs in free form in, for example, whey, other riboflavin derivatives can be isolated from bacteria and yeasts. A stereoisomer of riboflavin which is likewise suitable according to the invention is the lyxoflavin which can be isolated from fishmeal or liver and which carries a D-arabityl radical instead of the D-ribityl. Preference is given to using riboflavin or its derivatives in amounts of from 0.05 to 1% by weight, based on the total composition; Vitamin B3. This name often encompasses the compounds nicotinic acid and nicotinamide (niacinamide). According to the invention, preference is given to nicotinamide, which is present in the compositions according to the invention preferably in amounts of from 0.05 to 1% by weight, based on the total composition; Vitamin $B_5$ (pantothenic acid and panthenol). Preference is given to using panthenol. Derivatives of panthenol which can be used according to the invention are, in particular, the esters and ethers of panthenol, and also cationically derivatized panthenols.

In a further preferred embodiment of the invention, it is also possible to use derivatives of 2-furanone with the general structural formula (I) instead of, and in addition to, pantothenic acid or panthenol:

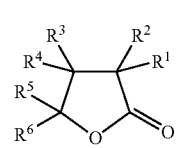

(I)

Preference is given to the 2-furanone derivatives in which the substituents $R^1$ to $R^6$, independently of one another, are a hydrogen atom, a hydroxyl radical, a methyl, methoxy, aminomethyl or hydroxymethyl radical, a saturated or mono- or diunsaturated, linear or branched $C_2$-$C_4$-hydrocarbon radical, a saturated or mono- or diunsaturated, branched or linear mono-, di- or trihydroxy-$C_2$-$C_4$-hydrocarbon radical or a saturated or mono-, or diunsaturated, branched or linear mono-, di- or triamino-$C_2$-$C_4$-hydrocarbon radical. Particularly preferred derivatives are the substances also available commercially dihydro-3-hydroxy-4,4-dimethyl-2 (3H)-furanone with the trivial name pantolactone (Merck), 4-hydroxymethyl-γ-butyrolactone (Merck), 3,3-dimethyl-2-hydroxy-γ-butyrolactone (Aldrich) and 2,5-dihydro-5-methoxy-2-furanone (Merck), where all stereoisomers are expressly included. The 2-furanone derivative which is exceptionally preferred according to the invention is pantolactone (dihydro-3-hydroxy-4,4-dimethyl-2(3H)-furanone), where, in formula (I), $R^1$ is a hydroxyl group, $R^2$ is a hydrogen atom, $R^3$ and $R^4$ are a methyl group and $R^5$ and $R^6$ are a hydrogen atom. The stereoisomer (R)-pantolactone is formed as pantothenic acid is broken down.

These compounds advantageously give the cosmetic composition according to the invention moisture-donating and skin-calming properties.

Said compounds of the vitamin $B_5$ type and the 2-furanone derivatives are preferably present in the compositions according to the invention, in a total amount of from 0.05 to 10% by weight, based on the total composition. Total amounts of from 0.1 to 5% by weight are particularly preferred. Vitamin $B_6$, which is not understood here as being a uniform substance, but the derivatives of 5-hydroxymethyl-2-methylpyridin-3-ol known under the trivial names pyridoxine, pyridoxamine and pyridoxal. Vitamin $B_6$ is present in the compositions according to the invention preferably in amounts of from 0.0001 to 1.0% by weight, in particular in amounts of from 0.001 to 0.01% by weight. Vitamin $B_7$ (biotin), also referred to as vitamin H or "skin vitamin". Biotin is (3aS,4S, 6aR)-2-oxohexahydrothienol[3, 4-d]-imidazole-4-valeric acid. Biotin is present in the compositions according to the invention preferably in amounts of from 0.0001 to 1.0% by weight, in particular in amounts of from 0.001 to 0.01% by weight.

Panthenol, pantolactone, nicotinamide and biotin are very particularly preferred according to the invention.

Auxiliaries and additives are understood as meaning substances which are suitable for improving the esthetic, performance and/or cosmetic properties, such as, for example, coemulsifiers, organic solvents, superfatting agents, stabilizers, antioxidants, waxes or fats, consistency-imparting agents, thickeners, tanning agents, vitamins, cationic polymers, biogenic active ingredients, preservatives, hydrotropic agents, solubilizers, dyes and fragrances.

For example, the following auxiliaries and additives may be used: allantoin, aloe vera, bisabolol, ceramides and pseudoceramides, antioxidants advantageously improve the stability of the compositions according to the invention. Antioxidants are, for example, amino acids (e.g. glycine, histidine, tyrosine, tryptophan) and derivatives thereof, imidazole and imidazole derivatives (e.g. urocanic acid), peptides, such as, for example, D,L-carnosine, D-carnosine, L-carnosine and derivatives thereof (e.g. anserine), carotenoids, carotenes (e.g. α-carotene, β-carotene, lycopene) and derivatives thereof, lipoic acid and derivatives thereof (e.g. dihydrolipoic acid), aurothioglucose, propylthiouracil and further thio compounds (e.g. thioglycerol, thiosorbitol, thioglycol acid, thioredoxin, glutathione, cysteine, cystine, cystamine and the glycosyl, N-acetyl, methyl, ethyl, propyl, amyl, butyl, lauryl, palmitoyl, oleyl, γ-linoleyl, cholesteryl and glyceryl esters thereof), and salts thereof, dilauryl thiodipropionate, distearyl thiodipropionate, thiodipropionic acid and derivatives thereof (esters, ethers, peptides, lipids, nucleotides nucleosides and salts), and sulfoximine compounds (e.g. buthionine sulfoximine, homocysteine sulfoximine, buthionine sulfones, penta-, hexa-, heptathionine sulfoximine) in very low tolerated doses (e.g. pmol/kg to μmol/kg), also metal chelating agents (e.g. α-hydroxy fatty acids, EDTA, EGTA, phytic acid, lactoferin), α-hydroxy acids (e.g. citric acid, lactic acid, malic acid), humic acids, bile acid, bile extracts, gallic esters (e.g. propyl, octyl and dodecyl gallate), flavonoids, catechins, bilirubin, biliverdin and derivatives thereof, unsaturated fatty acids and derivatives thereof (e.g. γ-linolenic acid, linoleic acid, arachidonic acid, oleic acid), folic acid and derivatives thereof, hydroquinone and derivatives thereof (e.g. arbutin), ubiquinone and ubiquinol, and derivatives thereof, vitamin C and derivatives thereof (e.g. ascorbyl palmitate, stearate, dipalmitate, acetate, Mg ascorbyl phosphates, sodium and magnesium ascorbate, disodium ascorbyl phosphate and sulfate, potassium ascorbyl tocopheryl phosphate, chitosan ascorbate), isoascorbic acid and derivatives thereof, tocopherols and derivatives thereof (e.g. tocopheryl acetate, linoleate, oleate and succinate, tocophereth-5, tocophereth-10, tocophereth-12, tocophereth-18, tocophereth-50, tocophersolan), vitamin A and derivatives (e.g. vitamin A palmitate), the coniferyl benzoate of benzoin resin, rutin, rutinic acid and derivatives thereof, disodium rutinyl disulfate, cinnamic acid and derivatives thereof (e.g. ferulic acid, ethyl ferulate, caffeic acid), kojic acid, chitosan glycolate and salicylate, butylhydroxytoluene, butylhydroxyanisole, nordihydroguaiacic acid, nordihydroguaiaretic acid, trihydroxybutyrophenone, uric acid and derivatives thereof, mannose and derivatives thereof, zinc and zinc derivatives (e.g. ZnO, $ZnSO_4$), selenium and selenium derivatives (e.g. selenomethionine), stilbenes and stilbene derivatives (e.g. stilbene oxide, trans-stilbene oxide). According to the invention, suitable derivatives (salts, esters, sugars, nucleotides, nucleosides, peptides and lipids), and mixtures of these specified active ingredients or plant extracts (e.g. teatree oil, rosemary extract and rosemarinic acid), which comprise these antioxidants can be used. Preferred lipophilic, oil-soluble antioxidants from this group are tocopherol and derivatives thereof, gallic esters, flavonoids and carotenoids, and butylhydroxytoluene/anisole. Preferred water-soluble antioxidants are amino acids, e.g. tyrosine and cysteine and derivatives thereof, and also tannins, in particular those of vegetable origin. The total amount of the antioxidants in the cosmetic compositions according to the invention is 0.001-20% by weight, preferably 0.05-10% by weight, in particular 0.1-5% by weight and very particularly preferably 0.1 to 2% by weight; triterpenes, in particular triterpene acids, such as ursolic acid, rosemarinic acid, betulinic acid, boswellic acid and bryonolic acid; monomers catechins, particularly catechin and epicatechin, leukoanthocyanidins, catechin polymers (catechin tannins), and gallotannins; thickeners, e.g. gelatins, plant gums, such as agar agar, guar gum, alginates, xanthan gum, gum arabic, karaya gum or carob comflour, natural and synthetic clays and sheet silicates, e.g. bentonite, hectorite, montmorillonite or Laponite®, completely synthetic hydrocolloids, such as, for example, polyvinyl alcohol, and also Ca, Mg or Zn soaps of fatty acids; plant glycosides; structurants, such as maleic acid and lactic acid; dimethyl isosorbide; alpha-, beta- and gamma-cyclodextrins, in particular for stabilizing retinol; solvents, swelling and penetration substances, such as ethanol, isopropanol, ethylene glycol, propylene glycol, propylene glycol monoethyl ether, glycerol and diethylene glycol, carbonates, hydrogencarbonates, guanidines, ureas, and primary, secondary and tertiary phosphates; perfume oils, pigments, and dyes for coloring the composition; substances for adjusting the pH, e.g. α- and β-hydroxycarboxylic acids; complexing agents, such as EDTA, NTA, β-alaninediacetic acid and phosphonic acids; opacifiers, such as latex, styrene/PVP and styrene/acrylamide copolymers; pearlizing agents, such as ethylene glycol mono- and distearate, and PEG-3 distearate; propellants, such as propane/butane mixtures, $N_2O$, dimethyl ether, $CO_2$ and air.

The addition of allantoin, bisabolol and/or aloe vera, also in the form of extracts, to the cosmetic compositions according to the invention further improves the skin-calming, moisture-donating and skincare properties of the formulations and is therefore particularly preferred.

As further ingredients, the cosmetic composition according to the invention may comprise, in minor amounts, further surfactants which are compatible with the other ingredients. Typical examples of anionic surfactants are soaps, alkylbenzenesulfonates, alkanesulfonates, olefinsulfonates, alkyl ether sulfonates, glycerol ether sulfonates, a-methyl ester sulfonates, sulfofatty acids, alkyl sulfates, fatty alcohol ether sulfates, glycerol ether sulfates, hydroxy mixed ether sulfates, monoglyceride (ether) sulfates, fatty acid amide (ether) sulfates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside sulfates, protein fatty acid condensates (in particular vegetable products based on wheat) and alkyl (ether) phosphates. If the anionic surfactants contain polyglycol ether chains, these may have a conventional homolog distribution, but they preferably have a narrowed homolog distribution. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers and mixed formals, optionally partially oxidized alk(en)yl oligo glycosides and glucuronic acid derivatives, fatty acid N-alkylglucamides, protein hydrolysates (in particular vegetable products based on wheat), polyol fatty acid esters, sugar esters, sorbitan esters, polysorbates and amine oxides. If the nonionic surfactants contain polyglycol ether chains, these may have a conventional homolog distribution, but they preferably have a narrowed homolog distribution. Typical examples of cationic surfactants are quaternary ammonium compounds and ester quats, in particular quaternized fatty acid trialkanolamine ester salts. Typical examples of amphoteric and zwitterionic surfactants are alkylbetaines, alkylamidobetaines, aminopropionates, aminoglycinates, imidazoliniumbetaines and sulfobetaines.

According to a further particularly preferred embodiment, the cosmetic composition according to the invention is used as sunscreen composition. The advantages resulting therefrom have already been explained in detail. Example 5 describes a basic formulation using the zinc oxide coated in accordance with the invention (with polyglycol diacid).

The use of the zinc oxide dispersions according to the invention is, in particular, likewise possible in hair cosmetics, such as shampoos, conditioners, rinses, hair tonics, hair gel, hair spray etc. In particular leave-on products, which remain on the hair and/or the scalp after having been applied are particularly highly suitable. The zinc oxide applied in this way to the scalp and the hair can thus also act there as UV protectant and/or develop its skin-calming effect on the scalp.

According to a preferred embodiment of the cosmetic composition according to the invention, the cosmetic composition is applied to the surface of the body to be treated and/or to be protected, i.e. topically. This application form is particularly advantageous since it is easy to handle, meaning that incorrect dosages are for the most part excluded. In addition, an additional care effect for the skin can be achieved. If only individual parts of the body are exposed to solar radiation, the sunscreen composition may also only be applied in a targeted manner to these parts of the body.

The present invention further provides for the use of zinc oxide surface-modified according to the invention or zinc oxide dispersions for UV protection. This is particularly advantageous since, due to the finely divided nature of the surface-modified zinc oxide and the good distribution, a particularly high UV absorption is achieved.

The present invention further provides for the use of zinc oxide surface-modified according to the invention or zinc oxide dispersions as antimicrobial active ingredient. The use of these particles is particularly advantageous for this intended use since, due to the finely divided nature of the particles and the large surface area resulting therefrom, the antimicrobial effect is considerably improved and, on the other hand, due to the good dispersing properties of the material, the zinc oxide is present in finely divided form. The zinc oxide can thus be used without problems in various administration forms, such as, for example, creams, skin milk, lotions or tonics.

The present invention further provides a pharmaceutical composition which comprises a surface-modified zinc oxide or a zinc oxide dispersion. This pharmaceutical composition is identified by the fact that, due to the finely divided nature of the particles, the pharmaceutical effectiveness is considerably increased. This becomes evident from the results of example 3, and FIGS. 1 and 2. Moreover, the pharmaceutical composition according to the invention has the advantage that, due to the good long-term stability of the zinc oxide dispersions, which has already been described above, it is possible to dispense with the addition of stabilizers which prevent separation. The compatibility of the pharmaceutical composition is thus additionally increased.

EXAMPLES

Example 1

6.2 g of ZnO are suspended in 80 ml of THF in a 250 ml round-bottomed flask. To this dispersion are added dropwise 1.5 g of polyethylene glycol diacid 600 (Aldrich Prod. No. 40,703-8, Batch No. 24441-030), dissolved in 40 ml of THF. The mixture is then boiled under reflux for 30 minutes. It is then cooled to room temperature and the THF is decanted off. The solid is admixed with 100 ml of THF and stirred for 15 minutes. The THF is again decanted off and the modified ZnO is dried under reduced pressure. The surface-modified ZnO obtained in this way can be dispersed in water without after-treatment.

According to the particle size distribution determination by means of dynamic light scattering, 95% of the particles are smaller than 50 nm and the volume-averaged particle size is 27 nm.

Example 2

3.5 g (0.043 mol) of ZnO are suspended in 100 ml of THF in a 500 ml three-necked flask. To this suspension is added a solution of 2 g of 2-[2-(2-methoxyethoxy)ethoxy]acetic acid (Fluka Art. No. 64732, Batch No. RB13802) in 30 ml of THF. The reaction solution is heated to boiling and held at the temperature for 1 hour. Within this time only a slightly cloudy dispersion is formed. After cooling to room temperature, the solvent is distilled off. The resulting solid is dispersed in 100 ml of water, and the excess acid is separated off by dialysis. After the water has been distilled off under reduced pressure, the resulting solid is dried under reduced pressure.

The modified ZnO obtained in this way can be dispersed to primary particle size in water and also in methanol, ethanol, isopropanol, acetone, toluene without after-treatment.

According to the particle size distribution determination by means of XRD, 90% of the particles are smaller than 22 nm and the average volume-weighted particle size is about 14 nm.

Example 3

In this comparative experiment, the skin-calming effect of the surface-modified zinc oxide particles/dispersions according to the invention was investigated compared with other skin-calming active ingredients. The following substances were used for this purpose:
1. zinc oxide surface-modified with polyethylene glycol diacetic acid, in 0.5% strength dispersion in water;
2. zinc oxide surface-modified with polyethylene glycol diacetic acid, 2% strength dispersion in water;
3. without skin irritation—rinsed with water
4. with SDS irritation—rinsed with water
5. with SDS irritation—treated with a cortisone ointment
6. D-panthenol, 0.5% strength
7. D-panthenol, 2% strength
8. zinc oxide dispersion in accordance with DE 19907704, 0.5% strength
9. zinc oxide in accordance with DE 19907704, 2% strength
10. solvent of (8) and (9) in accordance with DE 19907704: ethylene glycol/water/triethanolamine Formulations 1 and 2 specified above correspond to the zinc oxide dispersions according to the invention. These formulations were tested with regard to their skin-calming effect in vitro on an epidermis model and compared with the effect of D-panthenol in two different concentrations (formulations 6 and 7), and with a zinc oxide dispersion prepared in accordance with DE 19907704 (formulations 8 and 9).

Figure 2:
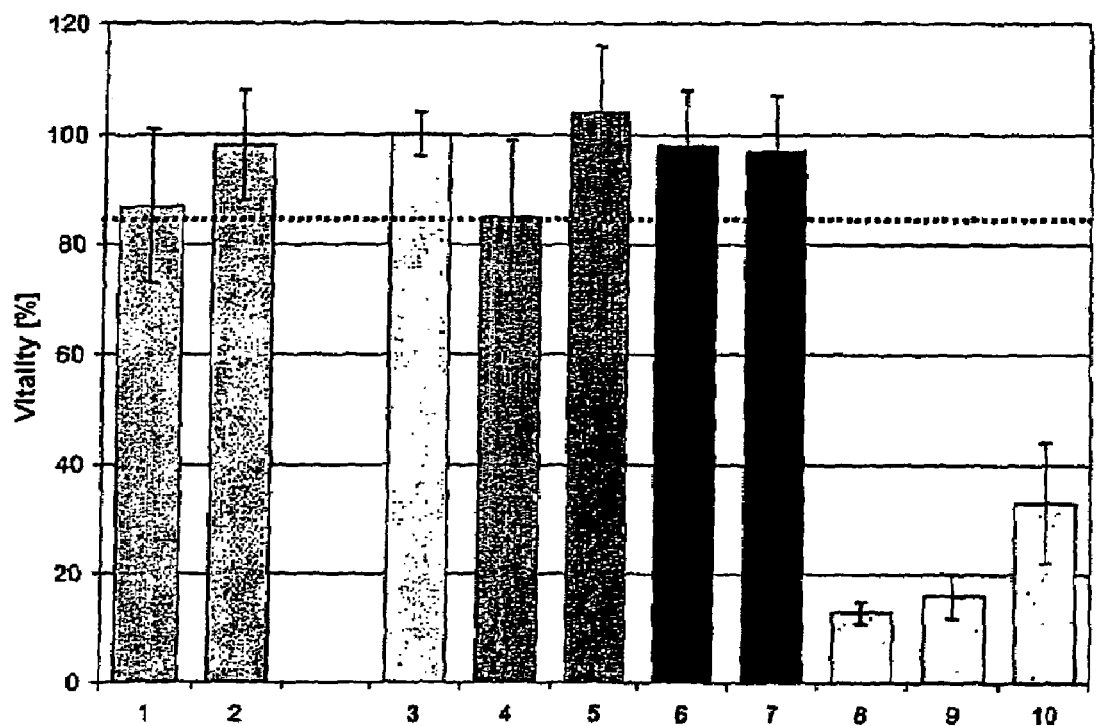
FIG. 2: shows vitality of the skin cultures after predamage for 1 hour with SDS 0.16% and subsequent incubation for 20 hours with the test substances (relative to the negative control water/water=100%).

The epidermis model used was the 3-dimensional EPI-DERM® model (Martek, USA). To trigger a skin irritation, the model was incubated with a surfactant (0.16% SDS=sodium dodecyl sulfate) for 1. hour. After the SDS had been rinsed off, treatment with the test substances was carried out. As an internal positive control, cortisone cream was entrained, which was applied accordingly after SDS irritation. For the surfactant control, the models were treated after SDS damage with demineralized water or solvent instead of the test substances, for the negative control, the treatment was carried out only with demineralized water instead of surfactant or test substance. A further incubation time of 20 h was carried out, after which the vitality of the model was tested in the MTT test (Journal of Immunological Methods, 65 (1983) 55-63), and the release of the inflammation mediator IL-1α was determined by means of ELISA (enzyme linked immuno sorbent assay). The results are shown in FIG. 1. Here, a high release of interleucin-1α means a small reduction in skin irritation, and a low release means a good skin-calming effect. In this comparison test, the zinc oxide dispersions according to the invention exhibit a very good skin-calming effect. Formulations 8 and 9 produce no reliable results with regard to their skin-calming effect since the solvent given in the description of DE 19907704 by itself led to considerable damage to the cells in the skin model. This can be seen in FIG. 2, which summarizes the results of the vitality determination according to the MTT test.

Example 4

Production of a Zinc Oxide Layer on a Glass Substrate.

500 µl of a 20% strength dispersion of zinc oxide surface-modified with polyethylene glycol diacid 600 in ethanol are applied uniformly to a round glass wafer (Corning 1737 F) with the activation of the spin coater. The speed program is adjusted such that the speed remains at 500 min$^{-1}$ for 5 s, while the dispersion is sprayed onto the substrate. The speed is then increased to 4000 min$^{-1}$ over an interval of 10 s and this speed is maintained for 20 s. It is then slowed down again to 0 min$^{-1}$.

The coated substrate is then heated for one hour in an air atmosphere in a muffle furnace at 350° C. (dT/dt=1° C./min).

The layer thickness is determined at 200 nm using a profilometer. The evaluation of the average particle size via the statistical evaluation of a scanning electron micrograph gives a value of 30 nm. The transmission in the visual region (400-800 nm) is 98.9%. The specific electrical resistance was determined via a 4-point measurement as 1.1*10$^{-4}$ □cm.

Example 5

The following components were processed together to give a sunscreen composition:

| Constituent | % by wt. |
| --- | --- |
| Cetiol OE (di-n-octyl ether) | 10 |
| Cetiol S (diisooctylcyclohexane) | 10 |
| Lanette O (cetylstearyl alcohol) | 4.5 |
| Eumulgin B2 (polyoxyethylene-20-cetylstearyl alcohol | 2 |
| Monomuls 60-35C | 2 |
| (monoglyceride of palm fatty acid, hydrogenated) | |
| Baysilon M 350 (silicone oil) | 0.5 |
| Phenonip (preservative) | 1 |
| Zinc oxide (surface-modified with isostearic acid) | 8 |
| Zinc oxide (surface-modified with polyglycol diacid) | 8 |
| Distilled water | ad 100 |

Preparation of Component A:

The apparatus used for the preparation consists of a beaker, propeller stirrer and a silicone bath with heating plate. The emulsifiers and the Baysilon oil are initially introduced into the beaker and heated to 85-90° C. The hydrophobic surface-modified zinc oxide (surface-modified with isostearic acid) is dispersed in one of the cosmetic oils or in a mixture of the cosmetic oils (Cetiol) using a magnetic stirrer. The zinc oxide dispersion is then added to the emulsifier melt. Water preheated to 85-100° C. is then added. The mixture is after-stirred for about 10 minutes at 85-90° C. and then cooled. During the cooling, the preservative was added at about 40° C. and vigorously stirred in.

Preparation of a Sun Cream

To prepare the sun cream, the amount of hydrophilically surface-coated zinc oxide (surface-modified with polyglycol diacid) given above is dispersed in the specified amount of water with stirring and heated to 40° C. Component A is then added to this dispersion with vigorous stirring. The cream was then cooled with stirring.

The disclosures of each patent, patent application, and publication cited or described in this document are hereby incorporated herein by reference, in their entireties.

Various modifications of the invention, in addition to those described herein, will be apparent to those skilled in the art from the foregoing description. Such modifications are also intended to fall within the scope of the appended claims.

What is claimed is:

1. A composition comprising:
   particles of zinc oxide coated with an oligo- or polyethylene glycol acid; and
   a solvent with a dipole moment greater than 0.35 µ/D.

2. The composition of claim 1, wherein the zinc oxide particles have a diameter of 1-200 nm.

3. The composition of claim 1, wherein the zinc oxide particles have a diameter of 2-50 nm.

4. The composition of claim 1, wherein the oligo- or polyethylene glycol acid has a formula:

R—CH$_2$—(O—CH$_2$—CH$_2$)$_n$—O—CH$_2$—COOH wherein:
n is an integer from 0 to 40; and
R is H, CH$_3$, C$_2$H$_5$, C$_3$H$_7$, CH(CH$_3$)$_2$, OH, NH$_2$, COOH, CONH$_2$, CO$_2$CH$_3$, CO$_2$C$_2$H$_5$, CO$_2$C$_3$H$_7$ or CO$_2$CH(CH$_3$)$_2$.

5. The composition of claim 4, wherein R is COOH.

6. The composition of claim 1, wherein the oligo- or polyethylene glycol acid is polyethylene glycol diacid 600.

7. The composition of claim 1, wherein the oligo- or polyethylene glycol acid is 2-[2-(2-methoxyethoxy)ethoxy] acetic acid.

8. The composition of claim 1, wherein the composition forms stable dispersions.

9. The composition of claim 8, wherein the composition is redispersible in polar organic solvents or water.

10. A method for making zinc oxide redispersible in polar organic solvents or water, comprising:
   suspending zinc oxide in a solvent with a dipole moment greater than 0.35 μ/D; and
   adding an oligo- or polyethylene glycol acid to form particles of zinc oxide coated with an oligo- or polyethylene glycol acid.

11. The method of claim 10, wherein the solvent is an organic solvent.

12. The method of claim 11, wherein the organic solvent is at least one of methanol, ethanol, n-propanol, isopropanol, acetone, diethyl ether, dimethyl sulfoxide, tetrahydrofuran, methylene chloride, trichloromethane, ethanol, ethyl acetate, isobutyl acetate or toluene.

13. The method of claim 10, wherein the solvent is THF.

14. The method of claim 10, wherein the solvent is a polar solvent.

15. The method of claim 10, further comprising heating during the step of adding.

16. The method of claim 10, further comprising drying the particles.

17. The method of claim 10, further comprising removing the solvent by evaporation, freezing, freeze-drying, filtering, or drying.

18. A zinc oxide dispersion, comprising the composition of claim 1.

19. The zinc oxide dispersion of claim 18, wherein the dispersion has a content of dispersed zinc oxide of from 0.001 to 50% by weight.

20. The zinc oxide dispersion of claim 18, wherein the dispersion has a content of dispersed zinc oxide of from 0.1 to 10% by weight.

21. The zinc oxide dispersion of claim 18, wherein the dispersion is largely transparent.

* * * * *